US010546374B2

(12) United States Patent
Onishi et al.

(10) Patent No.: US 10,546,374 B2
(45) Date of Patent: Jan. 28, 2020

(54) SEM INSPECTION APPARATUS AND PATTERN MATCHING METHOD

(71) Applicant: Toshiba Memory Corporation, Minato-ku (JP)

(72) Inventors: Atsushi Onishi, Nagoya (JP); Kazuhiro Nojima, Yokkaichi (JP)

(73) Assignee: Toshiba Memory Corporation, Minato-ku (JP)

( * ) Notice: Subject to any disclaimer, the term of this patent is extended or adjusted under 35 U.S.C. 154(b) by 157 days.

(21) Appl. No.: 15/912,611

(22) Filed: Mar. 6, 2018

(65) Prior Publication Data

US 2019/0080445 A1    Mar. 14, 2019

(30) Foreign Application Priority Data

Sep. 11, 2017  (JP) .................................. 2017-174378

(51) Int. Cl.
*G06T 7/00* (2017.01)
*H01J 37/29* (2006.01)

(52) U.S. Cl.
CPC .... *G06T 7/001* (2013.01); *G06T 2207/10061* (2013.01); *G06T 2207/30148* (2013.01); *H01J 37/29* (2013.01); *H01J 2237/2817* (2013.01)

(58) Field of Classification Search
CPC ......... G06T 2207/30148; G06T 7/0006; G06T 2207/10061; G06T 7/001; G03F 1/84; G03F 7/70625; H01J 2237/2817
See application file for complete search history.

(56) References Cited

U.S. PATENT DOCUMENTS

| | | | | |
|---|---|---|---|---|
| 4,498,018 A | * | 2/1985 | Lofmark | ................ H04B 1/581 307/17 |
| 6,366,688 B1 | * | 4/2002 | Jun | .................... G01R 31/2886 250/311 |
| 7,116,817 B2 | | 10/2006 | Tanaka et al. | |
| 8,589,108 B2 | | 11/2013 | Nikaido | |

(Continued)

FOREIGN PATENT DOCUMENTS

| | | |
|---|---|---|
| JP | 3698075 | 9/2005 |
| JP | 4769320 | 9/2011 |
| JP | 4891036 | 3/2012 |

*Primary Examiner* — Jingge Wu
(74) *Attorney, Agent, or Firm* — Oblon, McClelland, Maier & Neustadt, L.L.P.

(57) ABSTRACT

According to one embodiment, an SEM inspection apparatus includes an arithmetic processor. The arithmetic processor acquires design data corresponding to an inspection region. The arithmetic processor obtains a resistance component between each of wiring lines included in the inspection region and a portion on a substrate connected thereto, on a basis of the design data. The arithmetic processor obtains a capacitance component between each of the wiring lines included in the inspection region and the portion on the substrate connected thereto, on a basis of the design data. The arithmetic processor color-codes the wiring lines included in the inspection region of the design data, on a basis of a combination of the resistance component and the capacitance component. The arithmetic processor corrects a coordinate deviation between an SEM image and the color-coded design data by performing pattern matching between the color-coded design data and the SEM image.

16 Claims, 11 Drawing Sheets

(56) References Cited

U.S. PATENT DOCUMENTS

| | | | |
|---|---|---|---|
| 2002/0153916 A1* | 10/2002 | Lee | H01L 23/544 324/759.02 |
| 2005/0045821 A1* | 3/2005 | Noji | G01N 23/225 250/311 |
| 2010/0202654 A1* | 8/2010 | Matsuoka | G03F 7/70616 382/100 |
| 2011/0077877 A1* | 3/2011 | Nikaido | G01R 31/307 702/58 |
| 2011/0234830 A1* | 9/2011 | Kiyota | H01L 27/14609 348/222.1 |
| 2013/0171751 A1* | 7/2013 | Guu | H01L 22/20 438/15 |
| 2017/0346159 A1* | 11/2017 | Xue | H01Q 5/314 |

* cited by examiner

| | | CAPACITANCE COMPONENT | | |
|---|---|---|---|---|
| | | ~10 μm² | 10~1000 μm² | 1000 μm²~ |
| RESISTANCE COMPONENT | P+/P-Well | 200 | 210 | 220 |
| | N+/N-Well | 180 | 190 | 200 |
| | P+/N-Well | 120 | 130 | 140 |
| | N+/P-Well | 80 | 100 | 120 |
| | Gate | 50 | 50 | 50 |

SEM INSPECTION APPARATUS AND PATTERN MATCHING METHOD

CROSS-REFERENCE TO RELATED APPLICATIONS

This application is based upon and claims the benefit of priority from Japanese Patent Application No. 2017-174378, filed on Sep. 11, 2017; the entire contents of which are incorporated herein by reference.

FIELD

An embodiment described herein relates generally to an SEM inspection apparatus and a pattern matching method.

BACKGROUND

For devices and wiring lines formed above a semiconductor substrate, a technique is known that inspects a difference from design data by using an inspection image picked up by a Scanning Electron Microscope (SEM) apparatus.

However, in the conventional technique, when the inspection image is compared with the design data, a consideration is given to voltage contrast, but no disclosure is included about performing pattern matching between the design data and the inspection image to correct the positional deviation between the design data and the inspection image picked up by the SEM inspection apparatus.

DETAILED DESCRIPTION

In general, according to one embodiment, an SEM inspection apparatus includes an arithmetic processor. The arithmetic processor operates to acquire an SEM image of an inspection region containing a defect of an inspection object including a plurality of wiring lines above a substrate. The arithmetic processor operates to acquire design data corresponding to the inspection region of the inspection object. The arithmetic processor operates to obtain a resistance component between each of the wiring lines included in the inspection region and a portion on the substrate connected thereto, on a basis of the design data. The arithmetic processor operates to obtain a capacitance component between each of the wiring lines included in the inspection region and the portion on the substrate connected thereto, on a basis of the design data. The arithmetic processor operates to color-code the wiring lines included in the inspection region of the design data, on a basis of a combination of the resistance component and the capacitance component. The arithmetic processor operates to correct a coordinate deviation between the SEM image and the color-coded design data by performing pattern matching between the color-coded design data and the SEM image.

An exemplary embodiment of an SEM inspection apparatus and a pattern matching method will be explained below in detail with reference to the accompanying drawings. The present invention is not limited to the following embodiment.

Figure 1:
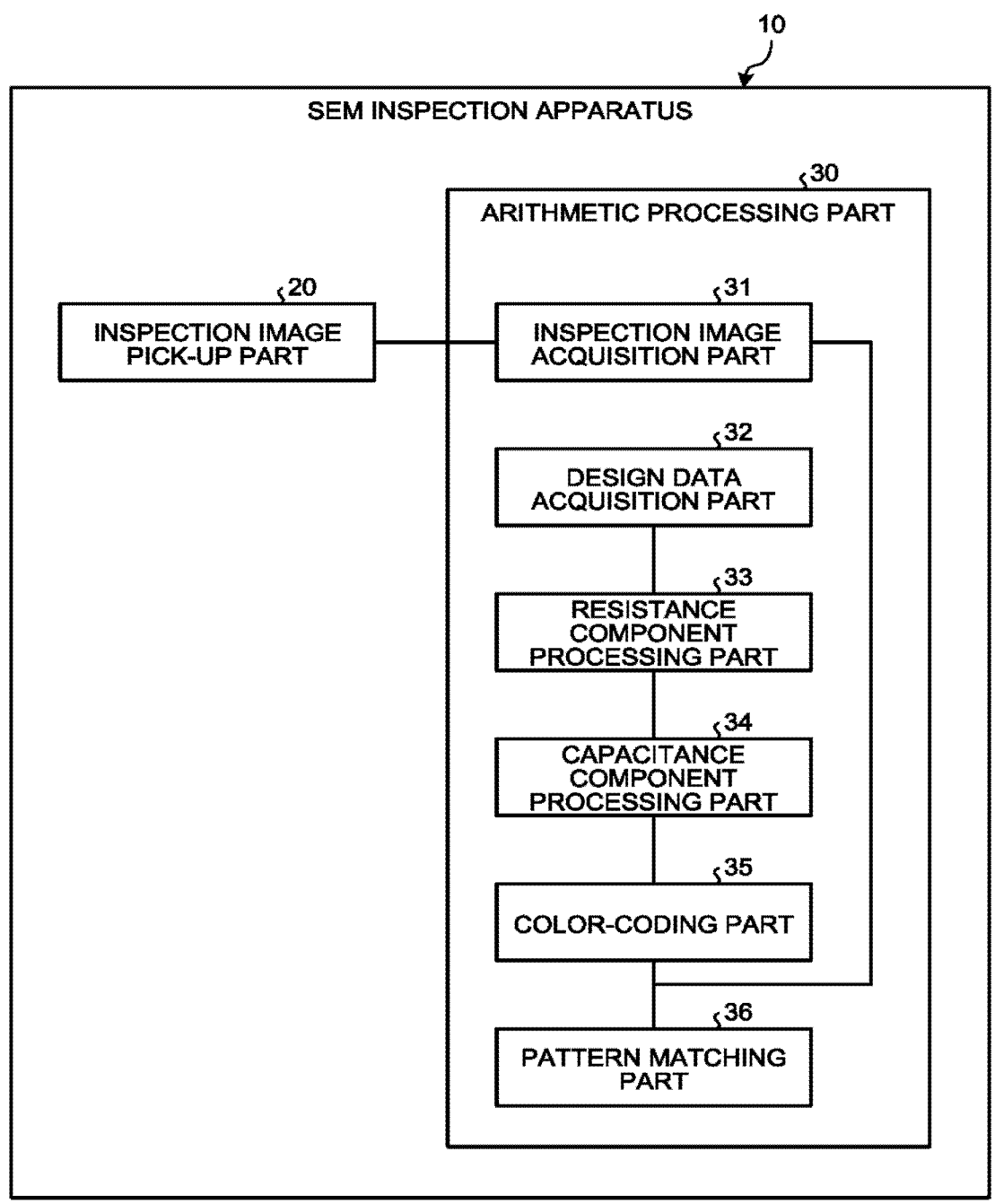
FIG. 1 is a block diagram schematically illustrating a functional configuration example of an SEM inspection apparatus according to an embodiment.

FIG. 1 is a block diagram schematically illustrating a functional configuration example of an SEM inspection apparatus according to an embodiment. The SEM inspection apparatus 10 includes an inspection image pick-up part 20 and an arithmetic processing part 30. The inspection image pick-up part 20 irradiates a semiconductor device treated as an inspection object with an electron beam to monitor the surface of the inspection object. The inspection image pick-up part 20 picks up an inspection image by using a detector. The detector detects secondary electrons that are released from the surface of the inspection object when the inspection object is irradiated with the electron beam. Alternatively, the detector detects reflection electrons that are generated from electrons reflected on the surface of the inspection object when the inspection object is irradiated with the electrons. The inspection image obtained by detecting the secondary electrons is a secondary electron image. The inspection image obtained by detecting the reflection electrons is a reflection electron image. Here, it is assumed that the inspection image pick-up part 20 picks up a secondary electron image. The inspection image pick-up part 20 is constituted of an SEM. Here, the inspection image pick-up part 20 images shot regions for performing inspection on a semiconductor device and a shot region serving as a reference, to determine an inspection region containing a defect among the shot regions. The inspection region thus determined is imaged by the inspection image pick-up part 20.

The arithmetic processing part 30 performs a pattern matching process between an inspection image picked up by the inspection image pick-up part 20 and layout data on the inspection object. The arithmetic processing part 30 includes an inspection image acquisition part 31, a design data acquisition part 32, a resistance component processing part 33, a capacitance component processing part 34, a color-coding part 35, and a pattern matching part 36. The arithmetic processing part 30 serves as an arithmetic processor for executing the functions of the inspection image acquisition part 31, the design data acquisition part 32, the resistance component processing part 33, the capacitance component processing part 34, the color-coding part 35, and the pattern matching part 36, as described later.

Figure 2:
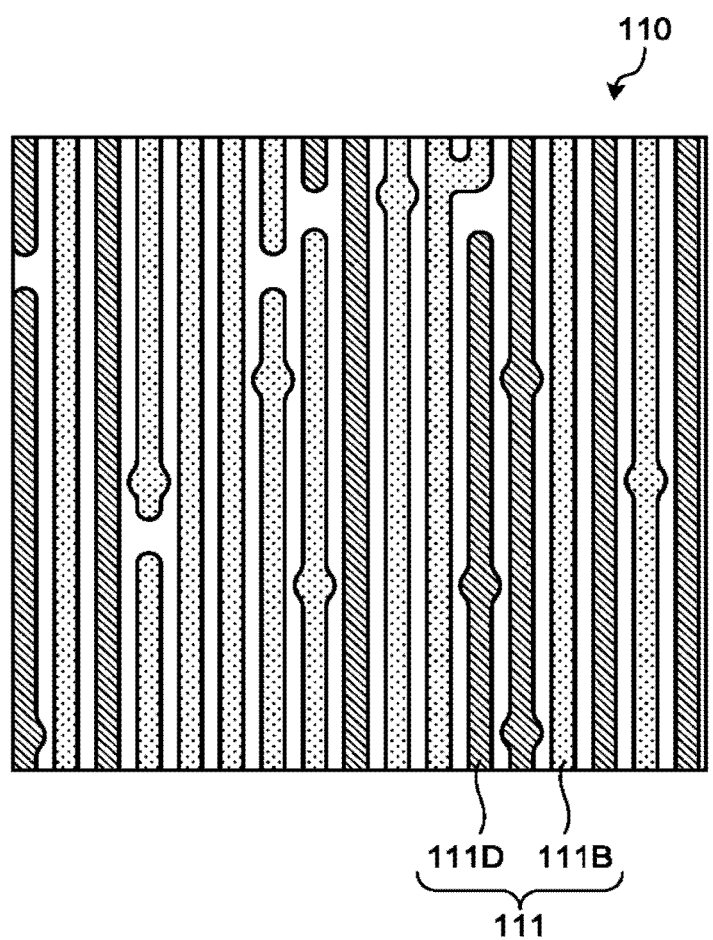
FIG. 2 is a diagram schematically illustrating an example of an inspection image.

The inspection image acquisition part 31 acquires an inspection image of an inspection region containing a defect, from the inspection image pick-up part 20. FIG. 2 is a diagram schematically illustrating an example of the inspection image. This inspection image 110 schematically shows a region where wiring lines 111 are arranged. As illustrated in FIG. 2, wiring lines 111B shown bright and wiring lines 111D shown dark are present in a mixed state.

The design data acquisition part 32 acquires design data of an inspection object imaged by the inspection image pick-up part 20. The inspection object includes a structure in which devices, such as a field effect transistor, are arranged on a substrate, such as a semiconductor substrate, and wiring lines are connected to the respective devices via contacts. Further, a plurality of layers is included on the substrate. Accordingly, the design data contains information on components including wiring lines, contacts, and devices, together with their arrangement positions, at respective layers on the inspection object, and connection information indicating the connection states of the components between the respective layers. Here, the components and their arrangement positions include the positions and conductivity types of wells formed in the substrate, and positions and conductivity types of diffusion layers formed in the wells and the substrate. Design data of this type is data created by Computer-Aided Design (CAD), for example.

Figure 3A:
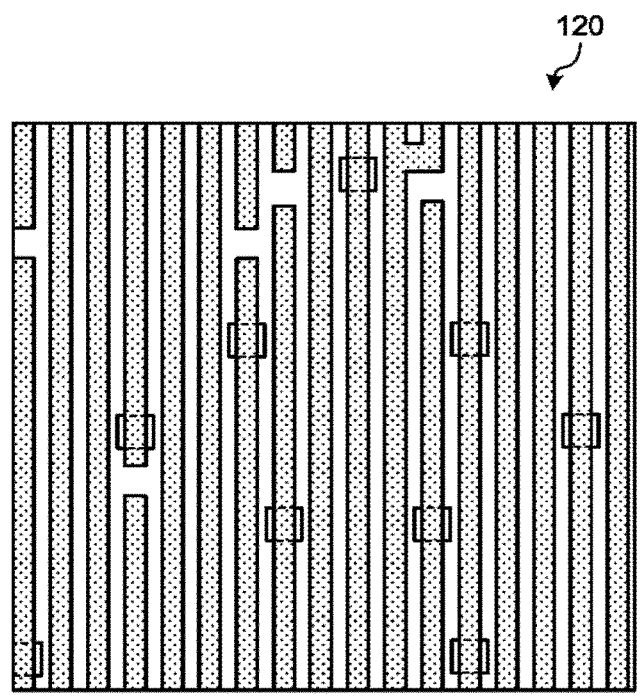
FIGS. 3A and 3B are diagrams illustrating an example of design data.
Figure 3B:
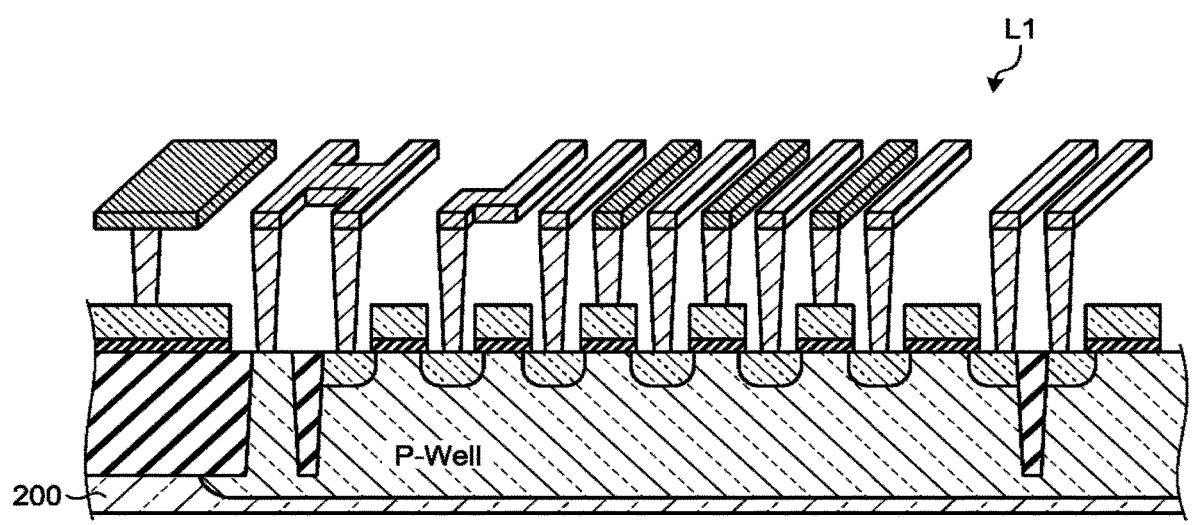

FIGS. 3A and 3B are diagrams illustrating an example of design data. FIG. 3A is a top view illustrating an example of design data on wiring lines at some layer. FIG. 3B is a perspective view schematically illustrating an example of design data in the height direction between wiring lines at some layer and the substrate. As illustrated in the top view of FIG. 3A, the design data 120 may indicate the arrangement of wiring lines at some layer. As illustrated in the perspective view of FIG. 3B, the design data 120 may indicate connection states from some layer L1 to the substrate 200.

The resistance component processing part 33 obtains a resistance component between each wiring line at some layer and a portion on the substrate connected thereto. Where the wiring lines are considered for each plug, as the resistance with respect to the substrate side is higher, the layer is charged more positive during the electron beam irradiation and thus becomes lower in brightness. Accordingly, the resistance components can be used to roughly classify the voltage contrast. The resistance components can be classified, on the basis of the connection destinations on the substrate connected from wiring lines under consideration. The connection destinations on the substrate connected from wiring lines can be classified into five types, which are (A) a P+-diffusion layer arranged in a P-well, (F) an N+-diffusion layer arranged in an N-well, (C) a P+-diffusion layer arranged in an N-well, (D) an N+-diffusion layer arranged in a P-well, and (E) a gate electrode.

FIGS. 4A to 4F are sectional views schematically illustrating an example of connection destinations on the substrate. In FIGS. 4A to 4F, a P-well 201 is arranged in the substrate 200, and an N-well 202 is arranged in part of the P-well 201. The P-well 201 is provided with an N-channel type field effect transistor 210 and a diffusion layer for contact. The N-channel type field effect transistor 210 includes a gate electrode 212 arranged on the P-well 201 through a gate insulating film 211, and N+-diffusion layers 213 arranged in the P-well 201 on the opposite sides of the gate electrode 212 in the gate length direction and serving as source/drain regions. The diffusion layer for contact is a P+-diffusion layer 220 formed in the P-well 201.

The N-well 202 is provided with a P-channel type field effect transistor 230 and a diffusion layer for contact. The P-channel type field effect transistor 230 includes a gate electrode 232 arranged on the N-well 202 through a gate insulating film 31, and P+-diffusion layers 233 arranged in the N-well 202 on the opposite sides of the gate electrode 232 in the gate length direction and serving as source/drain regions. The diffusion layer for contact is an N+-diffusion layer 240 formed in the N-well 202.

(A) P+-Diffusion Layer Arranged in P-Well

Figure 4A:
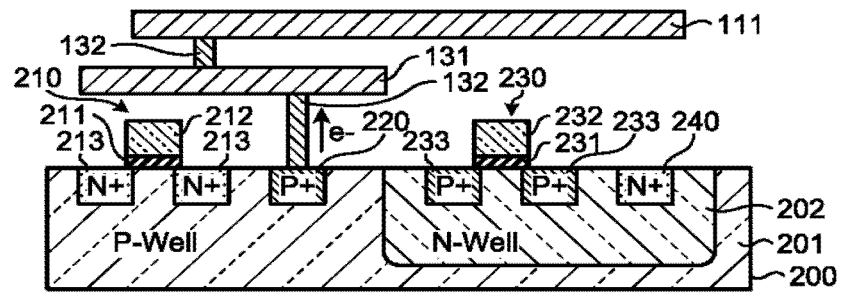
FIGS. 4A to 4F are sectional views schematically illustrating an example of connection destinations on a substrate.
Figure 4B:
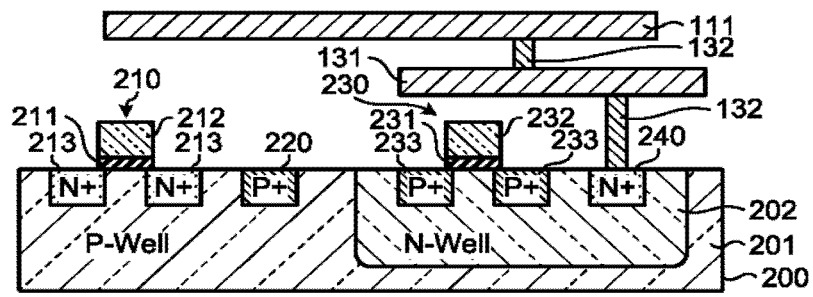

As illustrated in FIG. 4A, this case is exemplified by a structure in which a wiring line 111 is connected to the P+-diffusion layer 220 arranged in the P-well 201 via a wiring line layer 131 and a contact 132, which are present therebetween. When the inspection object is irradiated with an electron beam, there is no portion to be with a reverse bias on the route between the wiring line pattern and the substrate 200, and thus electrons are always supplied from the substrate 200 side to the wiring line 111 side. As a result, the wiring line 111 looks bright, when being monitored by a secondary electron image.

(B) N+-Diffusion Layer Arranged in Newell

Figure 4C:
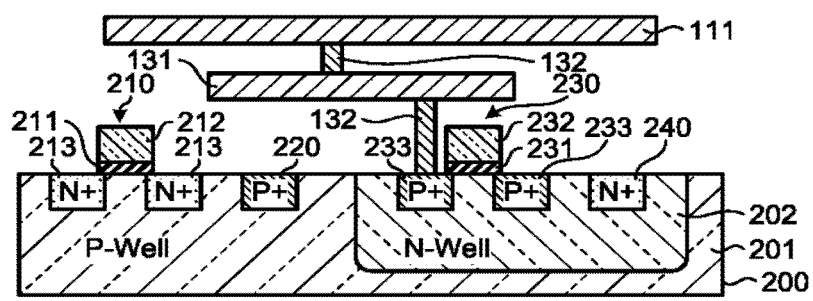
Figure 4D:
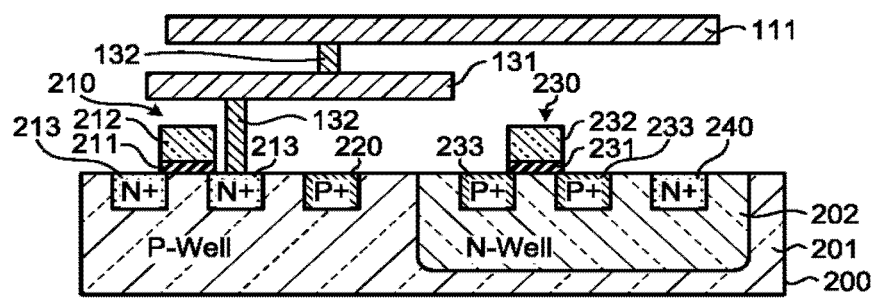
Figure 4E:
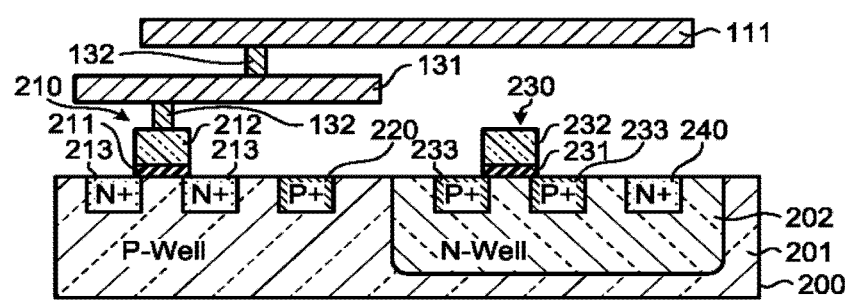

As illustrated in FIG. 4E, this case is exemplified by a structure in which a wiring line 111 is connected to the N+-diffusion layer 240 arranged in the N-well 202 via a wiring line layer 131 and a contact 132, which are present therebetween. When the inspection object is irradiated with an electron beam, there is a portion to he with a reverse bias on the route between the wiring line 111 and the substrate 200. Specifically, this portion is the boundary between the P-well 201 and the Newell 202. However, as the N-well 202 is formed as a sufficiently large part, electrons from the Newell 202 are supplied to the wiring line 111 side during imaging. Thus, there is no need to consider a portion to be with a reverse bias during imaging. As a result, the wiring line ill looks bright at a level next to the case of (A), when being monitored by a secondary electron image.

(C) P+-Diffusion Layer Arranged in Newell

As illustrated in FIG. 4C, this case is exemplified by a structure in which a wiring line 111 is connected to the P+-diffusion layer 233 of the P-channel type field effect transistor 230 arranged in the Newell 202 via a wiring line layer 131 and a contact 132, which are present therebetween. When the inspection object is irradiated with an electron beam, there is a portion to he with a reverse bias on the route between the wiring line 111 and the substrate 200, as in the case of (B). However, as the Newell 202 is formed as a sufficiently large part, electrons from the N-well 202 are supplied to the wiring line 111 side during imaging. Further, the boundary between the N-well 202 and the P+-diffusion layer 233 of the P-channel type field effect transistor 230 comes to be with a forward bias, electrons can move to the wiring line 111 side. In this case, the wiring line 111 locks bright at a level next to the case of (B), when being monitored by a secondary electron image.

(D) N+-Diffusion Layer Arranged in P-Well

As illustrated in FIG. 4D, this case is exemplified by a structure in which a wiring line 111 is connected to the N+-diffusion layer 213 of the N-channel type field effect transistor 210 arranged in the P-well 201 via a wiring line layer 131 and a contact 132, which are present therebetween. When the inspection object is irradiated with an electron beam, there is a portion to be with a reverse bias on the route between the wiring line 111 and the substrate 200. Specifically, this portion is the boundary between the P-well 201 and the N+-diffusion layer 213 of the N-channel type field effect transistor 210. Accordingly, electrons become difficult to be supplied to the wiring lines 111 side. As a result, the wiring line 111 looks far darker than the case of (C), when being monitored by a secondary electron image.

(E) Gate Electrode

As illustrated in FIG. 4E, this case is exemplified by a structure in which a wiring line 111 is connected to the gate electrode 212 of the N-channel type field effect transistor 210 provided on the P-well 201 via a wiring line layer 131 and a contact 132, which are present therebetween. When the inspection object is irradiated with an electron beam, there is no portion to be with a reverse bias on the route between the wiring line 111 and the substrate 200. However, the gate electrode 212 is in a floating state with respect to the substrate 200. Accordingly, electrons become difficult to be supplied to the wiring lines 111 side. As a result, the wiring line 111 looks darker than the case of (D), when being monitored by a secondary electron image. It should be noted that substantially the same is true also in a structure in which a wiring line 111 is connected to the gate electrode 232 of the P-channel type field effect transistor 230 provided on the N-well 202.

When the results described above are summarized, the brightness level relation obtained by the electron beam irradiation is expressed by the following formula (1):

Gate electrode<N+-diffusion layer/P-well<<P+-diffusion layer/N-well<N+-diffusion layer/N-well<P+-diffusion layer/P-well     (1)

Figure 4F:
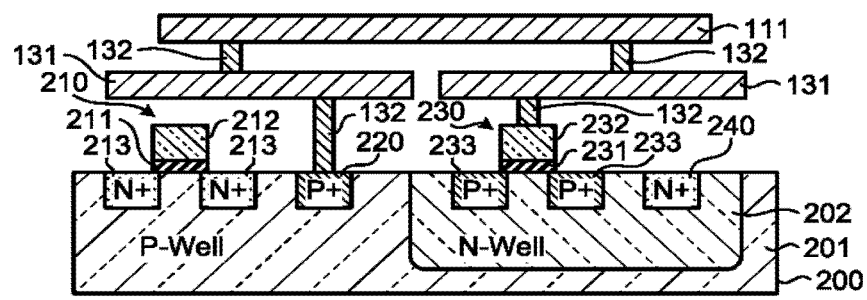

The resistance component processing part 33 identifies, from the design data, which one of the (A) to (E) described above is the connection destination on the substrate 200 connected from each wiring line 111. Here, there is a case where a plurality of connection destinations are present with respect to one wiring line 111. For example, the case of FIG. 4F is exemplified by a structure in which a wiring line 111 is connected to the P+-diffusion layer 220 arranged in the P-well 201 and the gate electrode 232 of the P-channel type field effect transistor 230 provided on the N-well 202 via wiring line layers 131 and contacts 132, which are present therebetween. In this case, of these connection destinations, the brighter connection destination is given priority. In the example of FIG. 4F, the P+-diffusion layer 220 arranged in the P-well 201 comes to be given priority, as a connection destination.

The capacitance component processing part 34 obtains a capacitance component between each wiring line 111 at some layer and a portion on the substrate 200 connected thereto. Specifically, where there is a PN junction between a wiring line 111 and the substrate 200, its junction area is obtained as a capacitance component. This is because the contrast of a wiring line 111 tends highly depend on a junction area connected thereto. In this example, a junction area is calculated for each wiring line 111 treated by the resistance component processing part 33.

Figures 5, 6:
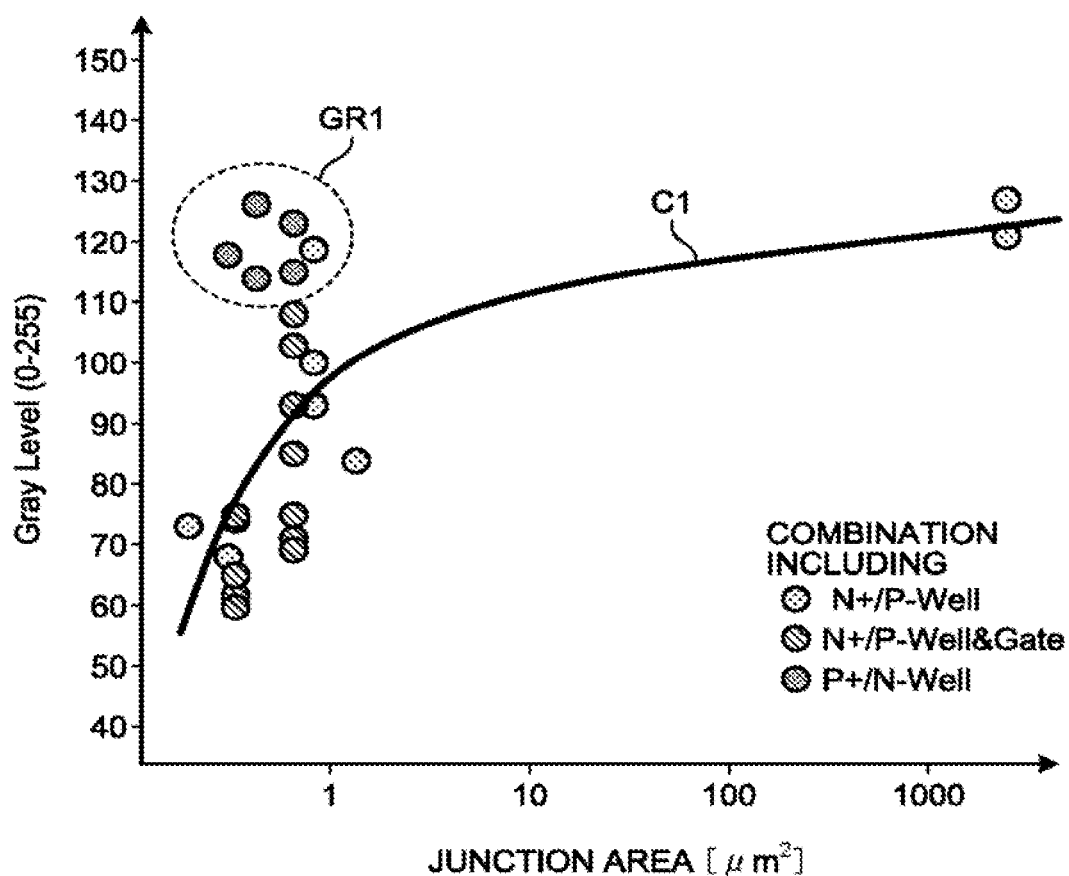
FIG. 5 is a graph illustrating an example of the relation between a junction area and brightness in a secondary electron image.
FIG. 6 is a diagram illustrating an example of color classification information according to the embodiment.

FIG. 5 is a graph illustrating an example of the relation between the junction area and brightness in a secondary electron image. The horizontal axis indicates the junction area of a PN junction present between a wiring line ill and the substrate 200 with a logarithmic scale. The vertical axis indicates the brightness of a wiring line 111 in the secondary electron image. Here, the brightness is indicated by correspondence to gray levels of 256 gradations.

The inspection image pick-up part 20 is used to pick up inspection images of regions each including one of the following wiring lines 111: a wiring line 111 connected to the N+-diffusion layer 213 arranged in the P-well 201; a wiring line Ill connected to the N+-diffusion layer 213 arranged in the P-well 201 and the gate electrode 212; and a wiring line 111 connected to the P+-diffusion layer 233 arranged in the N-well 202. Then, gray levels were obtained from the inspection images for the respective wiring lines 111.

As shown by a group GR1 in FIG. 5, wiring lines 111 each connected to the P+-diffusion layer 233 arranged in the N-well 202 exhibit a trend such that the gray level is high even if the junction area is small; this trend is different from those of the other wiring lines. On the other hand, as shown by an approximated curve C1, wiring lines 111 each connected to the N+-diffusion layer 213 arranged in the P-well 201, and wiring lines 1 each connected to the N+-diffusion layer 213 arranged in the P-well 201 and the gate electrode 212 exhibit a certain correlation between the junction area and the gray level. Specifically, as the junction area is smaller, the gray level is lower; as the junction area is larger, the gray level is higher. In this case of FIG. 5, for example, when the junction areas of the latter wiring lines come on the order of 1,000 $\mu m^2$, the gray levels becomes equivalent to those of wiring lines 111 each connected to the P+-diffusion layer 233 arranged in the N-well 202.

The color-coding part 35 performs color-coding to wiring lines 111 in accordance with color classification information, on the basis of the resistance components and capacitance components between the wiring lines 111 and the substrate 200, and thereby generates color-coded design data. The color classification information is information defining colors to be applied to wiring lines 111 contained in design data. These colors may be obtained by combinations of three primary colors of red, green, and blue, or may be formed of gray levels. For example, the color classification information may be obtained by combining a range of gray levels for respective resistance components acquired from inspection images and a range of gray levels for respective capacitance components acquired from inspection images.

FIG. 6 is a diagram illustrating an example of the color classification information according to the embodiment. This example is exemplified by a case where the colors of wiring line patterns are expressed by gray levels. In the color classification information, gray levels are established by combinations of a resistance component and a capacitance component. The resistance components may consist of five types, which are (A) a P+-diffusion layer arranged in a P-well (which is denoted as "P+/P-Well" in FIG. 6), (F) an N+-diffusion layer arranged in an N-well (which is denoted as "N+/N-Well" in FIG. 6), (C) a P+-diffusion layer arranged in an N-well (which is denoted as "P+/N-Well" in FIG. 6), (D) an N+-diffusion layer arranged in a P-well (which is denoted as "N+/P-Well" in FIG. 6), and (E) a gate electrode (which is denoted as "Gate" in FIG. 6). P+-diffusion layers each arranged in a P-well are set with gray levels of 200 to 220. N+-diffusion layers each arranged in an N-well are set with gray levels of 180 to 200. P+-diffusion layers each arranged in an N-well are set with gray levels of 120 to 140. N+-diffusion layers each arranged in a P-well are set with gray levels of 80 to 120. Gate electrodes are set with a gray level of 50.

The capacitance components may be represented by junction areas, which are classified into "less than 10 $\mu m^2$", "10 $\mu m^2$ or more and less than 1,000 $\mu m^2$", and "1,000 $\mu m^2$ or more" in the example of FIG. 6. For the respective resistance components, gray levels are established with respect to the respective classes of the junction area described above. Here, in the case of a resistance component associated with a gate electrode, as no junction area is present, the gray level is set to a constant value independently of the junction area in this example. Further, the color classification information described here is a mere example; thus, the embodiment is not limited to this. FIG. 6 illustrates a mere example. The gray level ranges assigned to resistance components, the capacitance component classified method, and the gray level ranges assigned to capacitance components may be arbitrarily set.

Figure 7:
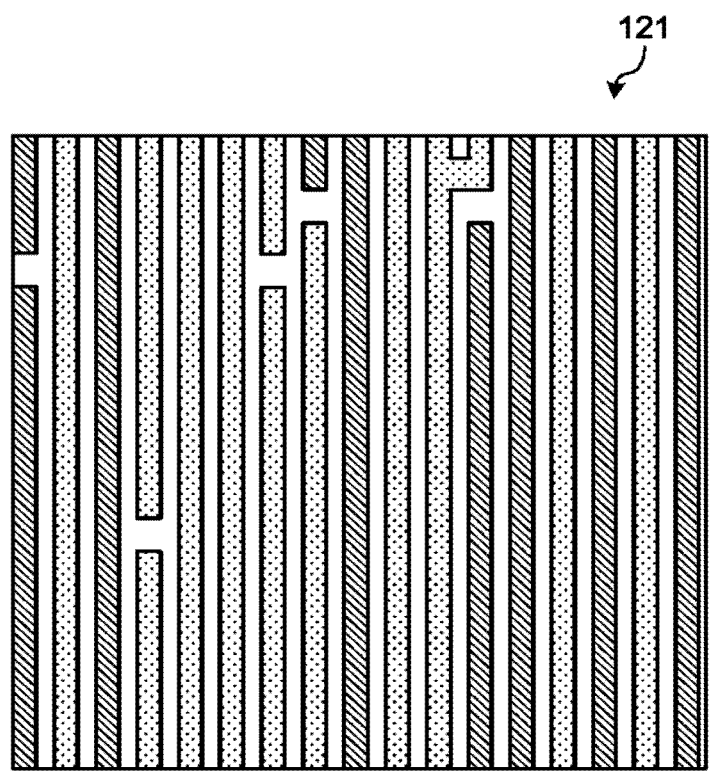
FIG. 7 is a diagram illustrating an example of color-coded design data according to the embodiment.

The color-coding part 35 obtains resistance components and capacitance components for, for example, the design data 120 illustrated in FIG. 3A, and applies colors to respective wiring lines 111 in accordance with the color classification information illustrated in FIG. 6. FIG. 7 is a diagram illustrating an example color-coded design data according to the embodiment. FIG. 7 illustrates color-coded design data 121 obtained by applying colors to the design data 120 of FIG. 3A.

The pattern matching part 36 performs pattern matching between the inspection image 110 and the color-coded design data 121, and corrects a coordinate deviation between the color-coded design data 121 and the inspection image 110. In general, the coordinate reference position used in the inspection image 110 and the coordinate reference position used in the color-coded design data 121 are different from each other. Accordingly, when the pattern matching is performed, for example, the position of a defect is used to calculate the deviation between the two coordinate reference positions as a positional deviation correction amount. Then, this positional deviation correction amount is used to correct the coordinates of the defect into correct coordinates on the design data 120 (the color-coded design data 121).

Figure 8:
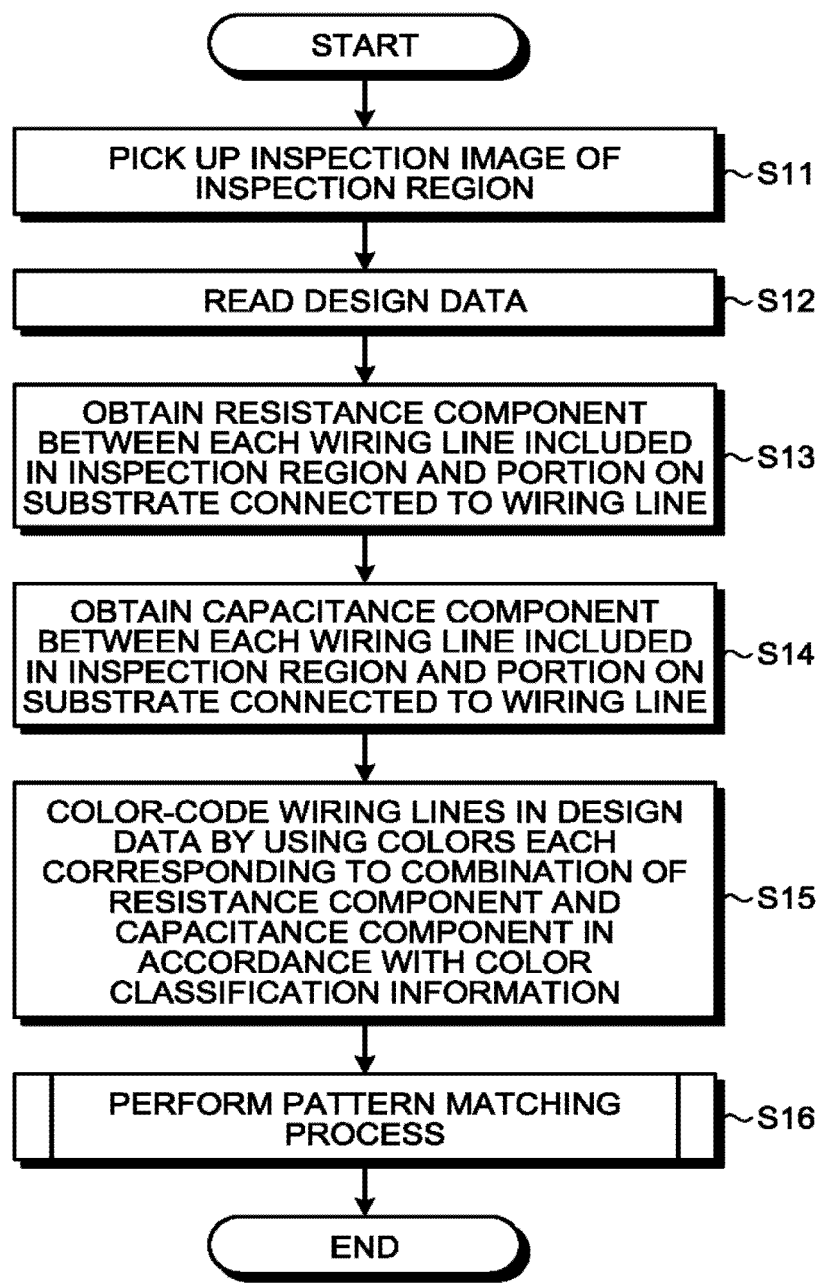
FIG. 8 is a flowchart illustrating an example of the process sequence of a pattern matching method according to the embodiment.

Next, an explanation will be given of a pattern matching process to be performed by the SEM inspection apparatus 10 having the structure described above. FIG. 8 is a flowchart illustrating an example of the process sequence of a pattern matching method according to the embodiment. First, a search is performed for the position of a defect among shot regions of a semiconductor device treated as an inspection object, to identify an inspection region containing the defect. At this time, in general, defects are not present at the same place in different shot regions. Accordingly, for example, imaging is performed to an inspection region inside the previous shot region and the corresponding inspection region inside the shot region to be now inspected, and these two images are compared with each other to recognise the place of a defect. Then, the inspection region is imaged by the inspection image pick-up part 20 of the SEM inspection apparatus 10 (step 311). Consequently, an inspection image 110 is obtained, as illustrated in FIG. 2.

Thereafter, the design data acquisition part 32 of the arithmetic processing part 30 reads design data 120 of the inspection object (step S12). For example, the design data 120 illustrated in FIG. 3A is obtained. Then, for each wiring line 111 included in the inspection region in the design data 120, the resistance component processing part 33 obtains a resistance component between this wiring line 111 and a portion on the substrate 200 connected thereto (step S13). Specifically, the connection destination on the substrate 200 connected from each wiring line 111 is obtained. As described above, this connection destination is any one of the five types, which are (A) a P+-diffusion layer arranged in a P-well, an N+-diffusion layer arranged in an N-well, (C) a P+-diffusion layer arranged in an N-well, (D) an N+-diffusion layer arranged in a P-well, and (E) a gate electrode.

Then, for each wiring line 111 included in the inspection region in the design data 120, the capacitance component processing part 34 obtains a capacitance component between this wiring line 111 and a portion on the substrate 200 connected thereto (step S14). Specifically, where there is a PN junction between the wiring line 111 and the substrate 200, the junction area of the PN junction is obtained.

Thereafter, the color-coding part 35 acquires a color corresponding to the combination of the resistance component and the capacitance component, from color classification information, to determine the color of each wiring line 111 in the design data 120, and color-codes the wiring lines 111 in the design data 120 (step S15). For example, a gray level corresponding to he combination of a resistance component obtained in step S13 and a capacitance component obtained in step S14 is obtained from the color classification information illustrated in FIG. 6, and the object wiring line 111 in the design data 120 is changed to the gray level thus obtained. This is performed to all the wiring lines 111 included in the inspection region, so that the color-coded design data 1 illustrated in FIG. 7 is obtained.

Figure 9:
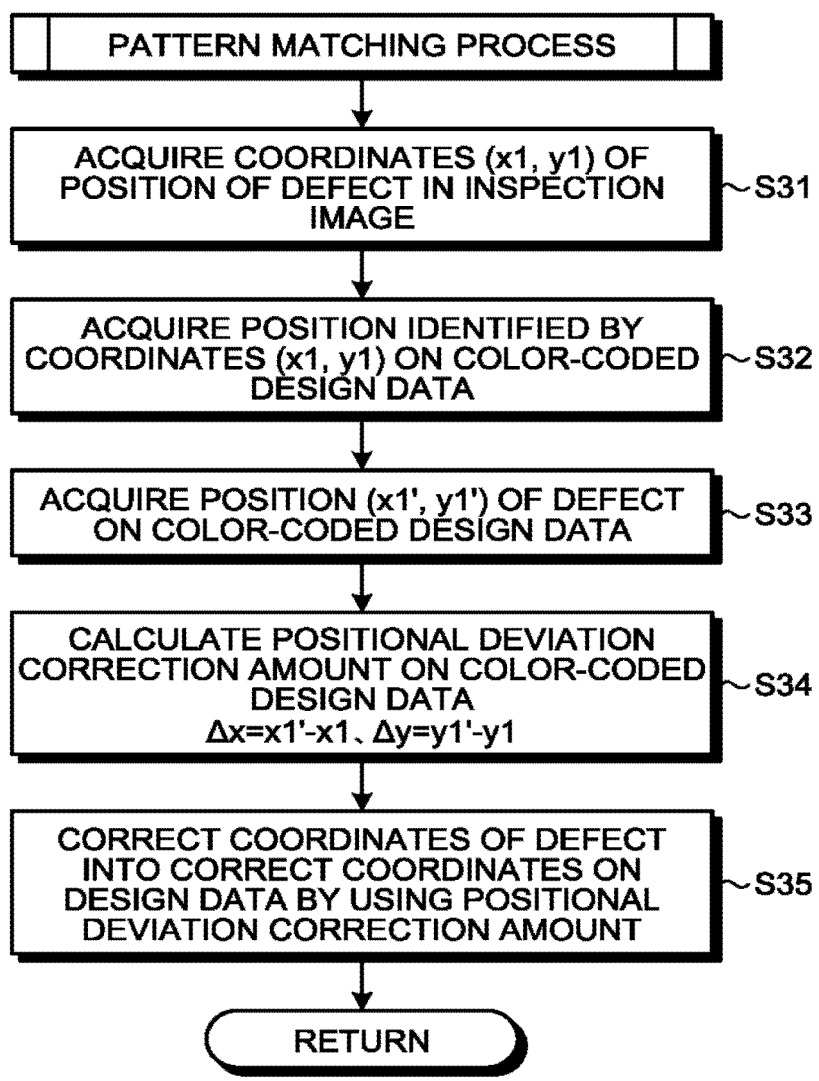
FIG. 9 is a flowchart illustrating an example of the sequence of a pattern matching process using the color-coded design data and an inspection image, according to the embodiment.
Figure 10A:
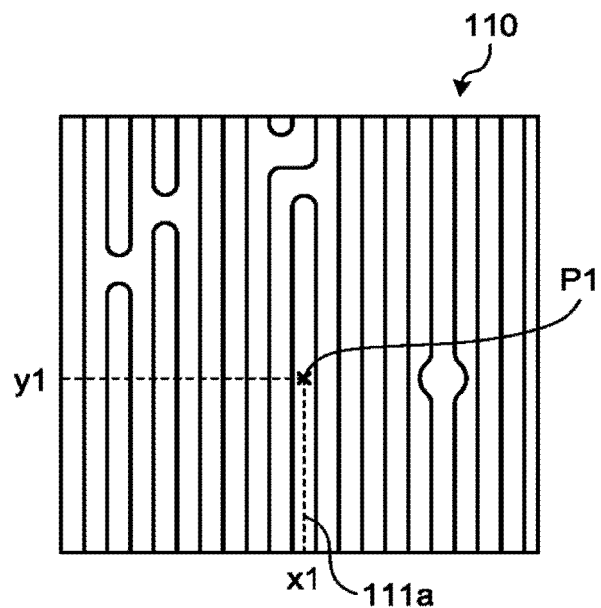
FIGS. 10A and 10B are diagrams illustrating the scheme of correction to a coordinate deviation between an inspection image and the color-coded design data, according to the embodiment.
Figure 10B:
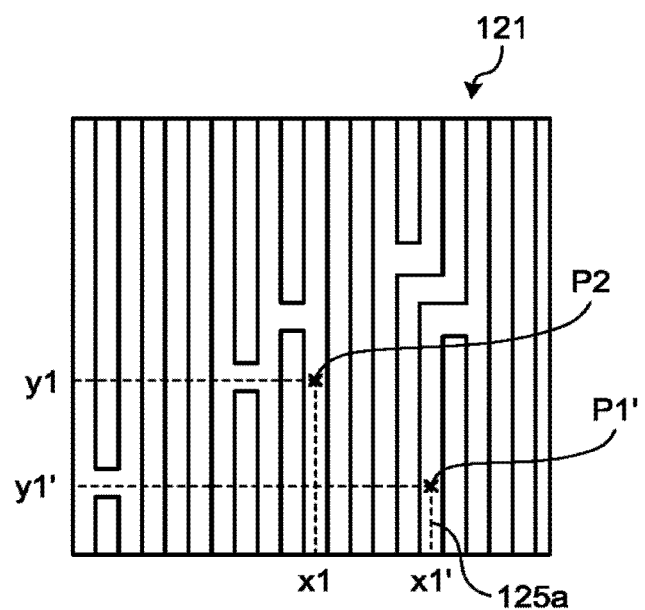

Then, the pattern matching part 36 performs a pattern matching process by using the color-coded design data 121 and the inspection image 110 (step 316). FIG. 9 is a flowchart illustrating an example of the sequence of the pattern matching process using the color-coded design data and the inspection image, according to the embodiment. FIGS. 10A and 10B are diagrams illustrating the scheme of correction to a coordinate deviation between the inspection image and the color-coded design data, according to the embodiment. FIG. 10A illustrates the inspection image, and FIG. 10B illustrates the color-coded design data. However, for the sake of easiness to understand the description, no color is applied in the inspection image 110 and the color-coded design data 121 in FIGS. 10A and 10B.

Here, first, as illustrated in FIG. 10A, the pattern matching part 36 acquires the coordinates (x1, y1) of the position P1 of a defect in the inspection image 110 (step S31). Then, as illustrated in FIG. 10B, the pattern matching part 36 acquires the position P2 identified by the coordinates (x1, y1) on the color-coded design data 121 (step S32). In general, as the coordinate reference position of the inspection image 110 and the coordinate reference position of the color-coded design data 121 are deviated from each other, the position P2 of the coordinates (x1, y1) on the color-coded design data 121 is different from the position of the defect.

Thereafter, as illustrated in FIG. 10B, the pattern matching part 36 acquires the position P1' (x1', y1') on the color-coded design data 121, which corresponds to the position P1 of the defect on the inspection image 110 (step 333). This is to identify the position of a wiring line 125a on the color-coded design data 121, which agrees with the position of a wiring line 111a with the defect present therein, for example, and is achieved on the basis of the shape of surrounding wiring lines and/or the arrangement of surrounding wiring lines.

Then, the pattern matching part 36 calculates a positional deviation correction amount ($\Delta x$, $\Delta y$) on the color-coded design data 121 (step S34). Here, $\Delta x = x1' - x1$ and $\Delta y = y1' - y1$ hold. Thereafter, the pattern matching part 36 corrects the coordinates of the defect into correct coordinates on the design data 120 by using the positional deviation correction amount (step S35). As a result, the pattern matching process ends.

Here, in the description described above, all of the wiring lines 111 are subjected to the color-coding by the color classification information to perform the pattern matching. However, all of the wiring lines do not necessarily have to be subjected to the color-coding. For example, only wiring lines 111 connected to the substrate 200, and particularly grounded wiring lines 111, may be subjected to the color-coding by the color classification information to perform the pattern matching. In this case, in the color classification information, for example, the color or gray level of wiring lines 111 each connected to a gate electrode is set to a color or gray level the same as that of the background of wiring lines 111 (which corresponds to interlayer insulating films). In this case, when an inspection image (secondary electron image) is picked up, wiring lines with low brightness are not treated as a pattern matching object, and thus the matching accuracy can be more improved.

Figure 11:
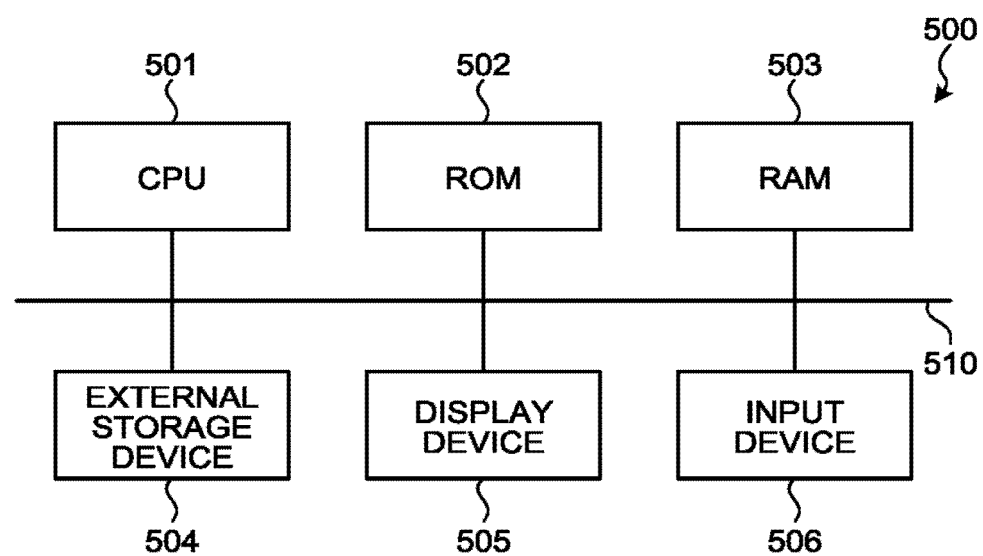
FIG. 11 is a block diagram schematically illustrating a hardware configuration example of an information processing device configured to execute the process of the pattern matching method.

FIG. 11 is a block diagram schematically illustrating a hardware configuration example of an information processing device configured to execute the process of the pattern matching method. The information processing device 500 has a configuration in which a Central Processing Unit (CPU) 501, a Read Only Memory (ROM) 502, a Random Access Memory (RAM) 503, an external storage device 504, such as a Hard Disk Drive (HDD), Solid State Drive (SSD), or Compact Disc (CD) drive device, a display device 505, such as a display, and input devices 506, such as a keyboard and a mouse, are connected to each other via a bus 510.

The pattern matching method described above is provided as a program. This program is provided in a state recorded in a computer-readable recording medium, such as a CD-ROM, flexible disk (FD), CD-R, Digital Versatile Disk (DVD), or a memory card, by a file in an installable format or executable format.

Alternatively, a program for executing the pattern matching method described above may be provided such that the program is stored in an information processing device connected to a network, such as the internet, and is downloaded via the network. Further, a program for executing the pattern matching method described above may be provided such that the program is provided or distributed via a network, such as the internet.

in the information processing device 500, this program is loaded in the RAM 503 and is executed by the CPU 501, so that the pattern matching method described with reference to FIGS. 8 and 9 is executed. The information processing device 500 corresponds to the arithmetic processing part 30 of FIG. 1.

In the embodiment, for each wiring line in the design data, a resistance component and a capacitance component are obtained, and a color is selected which corresponds to the combination of the resistance component and the capacitance component, in accordance with the color classification information. Then, wiring lines in the design data are colored by using colors thus selected. Further, pattern matching is performed between an inspection image picked up by an electron microscope and the color-coded design data to calculate a positional deviation amount of the design data with respect to the inspection image. As the color-coded design data is used in this way, the success rate of the pattern matching is improved. As a result, an effect is obtained that can precisely correct the coordinate deviation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An SEM inspection apparatus comprising an arithmetic processor, wherein the arithmetic processor operates
   to acquire an SEM image of an inspection region containing a defect of an inspection object including a plurality of wiring lines above a substrate,
   to acquire design data corresponding to the inspection region of the inspection object,
   to obtain a resistance component between each of the wiring lines included in the inspection region and a portion on the substrate connected thereto, on a basis of the design data,
   to obtain a capacitance component between each of the wiring lines included in the inspection region and the portion on the substrate connected thereto, on a basis of the design data,
   to color-code the wiring lines included in the inspection region of the design data, on a basis of combination of the resistance component and the capacitance component, and
   to correct a coordinate deviation between the SEM image and the color-coded design data by performing pattern matching between the color-coded design data and the SEM image.

2. The SEM inspection apparatus according to claim 1, wherein the arithmetic processor operates to classify resistance components on a basis of connection destinations on the substrate connected from the wiring lines to obtain the resistance component.

3. The SEM inspection apparatus according to claim 2, wherein each of the connection destinations is any one of a P+-diffusion layer arranged in a P-well, an N+-diffusion layer arranged in an N-well, a P+-diffusion layer arranged in an N-well, an N+-diffusion layer arranged in a P-well, and a gate electrode.

4. The SEM inspection apparatus according to claim 3, wherein the arithmetic processor operates to classify capacitance components, on a basis of junction areas of diffusion layers on the substrate, to which the wiring lines are connected to obtain the capacitance component.

5. The SEM inspection apparatus according to claim 4, wherein the arithmetic processor operates to color-code the wiring lines in the design data, in accordance with color classification information that defines colors to be applied to the wiring lines in the design data on a basis of combinations of the resistance components and the capacitance components.

6. The SEM inspection apparatus according to claim 5, wherein the color classification information has been prepared by acquiring a relation between the capacitance components and corresponding brightness in the SEM image, for each of the resistance components.

7. The SEM inspection apparatus according to claim 1, further comprising an inspection image pick-up part that picks up the SEM image of the inspection object.

8. The SEM inspection apparatus according to claim 1, wherein the SEM image is a secondary electron image.

9. A pattern matching method comprising:
   acquiring an SEM image of an inspection region containing a defect of an inspection object including a plurality of wiring lines above a substrate,
   acquiring design data corresponding to the inspection region of the inspection object,
   obtaining a resistance component between each of the wiring lines included in the inspection region and a portion on the substrate connected thereto, on a basis of the design data, obtaining a capacitance component between each of the wiring lines included in the inspection region and the portion on the substrate connected thereto, on a basis of the design data, color coding the wiring lines included in the inspection region of the design data, on a basis of a combination of the resistance component and the capacitance component, and correcting a coordinate deviation between the SEM image and the color-coded design data by performing pattern matching between the color-coded design data and the SEM image.

10. The pattern matching method according to claim 9, wherein, in the obtaining of the resistance component, resistance components are classified, on a basis of connection destinations on the substrate connected from the wiring lines.

11. The pattern matching method according to claim 10, wherein each of the connection destinations is any one of a P+-diffusion layer arranged in a P-well, an N+-diffusion layer arranged in an N-well, a P+-diffusion layer arranged in an N-well, an N+-diffusion layer arranged in a P-well, and a gate electrode.

12. The pattern matching method according to claim 11, wherein, in the obtaining of the capacitance component, capacitance components are classified, on a basis of junction areas of diffusion layers on the substrate, to which the wiring lines are connected.

13. The pattern matching method according to claim 12, wherein, in the color-coding, the wiring lines in the design data are color-coded, in accordance with color classification information that defines colors to be applied to the wiring lines in the design data on a basis of combinations of the resistance components and the capacitance components.

14. The pattern matching method according to claim 13, wherein the color classification information has been prepared by acquiring a relation between the capacitance components and corresponding brightness in the SEM image, for each of the resistance components.

15. The pattern matching method according to claim 9, further comprising picking up the SEM image of the inspection object.

16. The pattern matching method according to claim 9, wherein the SEM image is a secondary electron image.

* * * * *